US010881592B2

(12) United States Patent
Coulston et al.

(10) Patent No.: US 10,881,592 B2
(45) Date of Patent: Jan. 5, 2021

(54) CUCURBITURIL SUSPENSION COMPOSITIONS

(71) Applicant: AQDOT LIMITED, Pampisford (GB)

(72) Inventors: Roger Coulston, Pampisford (GB); David Diec, Pampisford (GB); Andrew Michael Howe, Pampisford (GB); Jose Martinez-Santiago, Pampisford (GB)

(73) Assignee: AQDOT LIMITED, Cambridge (GB)

( * ) Notice: Subject to any disclaimer, the term of this patent is extended or adjusted under 35 U.S.C. 154(b) by 0 days.

(21) Appl. No.: 16/328,216

(22) PCT Filed: Aug. 11, 2017

(86) PCT No.: PCT/GB2017/052380
§ 371 (c)(1),
(2) Date: Feb. 25, 2019

(87) PCT Pub. No.: WO2018/037209
PCT Pub. Date: Mar. 1, 2018

(65) Prior Publication Data
US 2019/0209444 A1    Jul. 11, 2019

(30) Foreign Application Priority Data
Aug. 24, 2016    (GB) .................... 1614458.6

(51) Int. Cl.
*A61K 8/04*    (2006.01)
*A61K 8/49*    (2006.01)
(Continued)

(52) U.S. Cl.
CPC .......... *A61K 8/044* (2013.01); *A61K 8/0241* (2013.01); *A61K 8/34* (2013.01); *A61K 8/4946* (2013.01);
(Continued)

(58) Field of Classification Search
CPC . A61K 8/044; A61K 8/34; A61K 8/73; A61K 8/8147; A61K 8/4946;
(Continued)

(56) References Cited

U.S. PATENT DOCUMENTS

| 5,942,217 A | 8/1999 | Woo et al. |
| 6,869,466 B2 * | 3/2005 | Day ................. C07D 487/22 95/205 |
| 2014/0238271 A1 | 8/2014 | Duncan et al. |

FOREIGN PATENT DOCUMENTS

| CN | 104086691 A | 10/2014 |
| WO | 2005/010004 A1 * | 2/2005 |

(Continued)

OTHER PUBLICATIONS

Oct. 25, 2016 Combined Search and Examination Report issued in British Patent Application No. 1614458.6.
(Continued)

*Primary Examiner* — Carlos A Azpuru
(74) *Attorney, Agent, or Firm* — Oliff PLC (57) ABSTRACT

Stable suspension compositions including cucurbiturils. More particularly, the stable suspension compositions including cucurbituril particles suspended in a medium. Also, the preparation of the suspension composition and a method of counteracting malodour including application of the suspension composition to a source of malodour.

24 Claims, 2 Drawing Sheets

(51) Int. Cl.
    *A61Q 13/00*     (2006.01)
    *A61Q 15/00*     (2006.01)
    *A61K 8/02*     (2006.01)
    *A61L 9/012*     (2006.01)
    *A61L 9/014*     (2006.01)
    *A61K 8/34*     (2006.01)
    *A61K 8/73*     (2006.01)
    *A61K 8/81*     (2006.01)

(52) U.S. Cl.
    CPC .............. *A61K 8/73* (2013.01); *A61K 8/8147* (2013.01); *A61L 9/012* (2013.01); *A61L 9/014* (2013.01); *A61Q 13/00* (2013.01); *A61Q 15/00* (2013.01); *A61K 2800/412* (2013.01); *A61K 2800/58* (2013.01)

(58) Field of Classification Search
    CPC .............. A61K 8/0241; A61K 2800/58; A61K 2800/412; A61L 9/014; A61L 9/012; A61L 9/01; A61Q 13/00; A61Q 15/00; B01J 13/00; C07D 487/22; C11B 9/00
    See application file for complete search history.

(56) References Cited

FOREIGN PATENT DOCUMENTS

| WO | 2005010004 A1 * | 2/2005 |
| WO | 2008/123685 A1 | 10/2008 |
| WO | 2014/077642 A1 | 5/2014 |
| WO | 2017/141030 A1 | 8/2017 |

OTHER PUBLICATIONS

Oct. 18, 2017 International Search Report issued in International Patent Application No. PCT/GB2017/052380.

Oct. 18, 2017 Written Opinion of the International Searching Authority issued in International Patent Application No. PCT/GB2017/052380.

J. Lagona, et al., "The Cucurbit[n]uril Family", Angewandte Chemie Int. Ed., vol. 44, pp. 4844-4870, 2005.

* cited by examiner

CUCURBITURIL SUSPENSION COMPOSITIONS

FIELD OF THE INVENTION

This invention relates to stable suspension compositions comprising cucurbiturils. More particularly, the invention relates to stable suspension compositions comprising cucurbituril particles suspended in a medium for use in counteracting malodour.

BACKGROUND

Malodours are often complex mixtures of different molecules having diverse chemistries and smells. The smell of malodour may be pungent and even minute amounts of such molecules can create uncomfortable impressions to consumers. Therefore, many strategies have been proposed to counteract malodours. Preventive methods involve killing the bacteria that are responsible for the generation of malodours or inhibiting their growth, either by applying biocides, biostatic agents or controlling the microclimatic conditions in the locus where bacteria proliferate. These methods are used for example in the axilla or other part of the human or pet body. Eliminative methods involve using chemically reactive molecules that bind to the malodour and neutralise it; oxidation (burning) and ionisation belong to eliminative methods. The disadvantage of all of these methods is that they involve agents that are not chemically or biologically inert, or environmentally neutral. In particular the use of biocides and reactive chemicals is subject to sanitary concerns. The by-products of ionisation and combustion may also be toxic and undesirable.

Alternatively, perfume and perfumery can be used to mask or combine the malodour in a way that the perception of the malodour by the consumer is reduced. However, complex malodours are difficult to mitigate by using such sensory methods, because of the diversity of smells involved.

Alternative methods to the preventive methods described above include suppression methods. Malodour suppression methods involve the use of absorbents and adsorbents materials. These materials may be environmentally friendly and in most cases have no noticeable odour. Malodour molecules are trapped in the pores of these materials and therefore their vapour pressure is depressed. However, these materials are generally not selective to malodour and may also bind desirable fragrance molecules. Furthermore, water vapours, such as those present in moist conditions, for example above 50% relative humidity, may displace the malodour which is then released back into the air.

Host molecules are a special class of absorbent materials, characterised in that each molecule has a well-defined cavity instead of a distribution of pores. Host-guest complexes have been used in the field of perfumery and for malodour counteracting. For example, U.S. Pat. No. 5,942,217 describes the use of an aqueous solution of cyclodextrin, more generally referred to as cyclic oligosaccharides, for neutralising malodour. Absorption of the malodour molecule in the cyclodextrin cavity results in efficient mitigation of malodour.

The action of cyclodextrin on the perception of both malodours and perfumes depends strongly on the activity of water in the system. This action reflects complex equilibria involving water, fragrance and malodour inclusion in the cyclodextrin cavity. Hence, the apparent host-guest binding constant may vary for both fragrances and malodours, depending on the concentration of water in the system. The poor predictability of such, essentially non-equilibrium effects, is a source of recurring difficulties for the perfumer. The poor selectivity of cyclodextrin binding and release with respect to fragrances and malodours is a disadvantage. Although this effect can be beneficial in the context of the controlled release of a desirable odour, it becomes very unsatisfactory if the guest molecule released is a malodour.

Another disadvantage of cyclodextrins is the tendency of these carbohydrate-derived materials to become sticky at low water levels or with decreasing water activity. This can lead to, for example, an undesirable "tacky" feeling on the skin. Finally, as is usually the case with aqueous carbohydrate solutions, aqueous cyclodextrin solutions must be preserved against micro-organism invasion using significant amounts of preservatives.

In view of the disadvantages associated with cyclodextrin, alternative host-guest systems are desirable which overcome these problems. In U.S. Pat. No. 6,869,466, a method is described to bind a gas or a volatile molecule to a cucurbituril to form an inclusion complex as well as steps for releasing at least some of the bound gas or volatile compounds. Trapping a malodorous compound is mentioned as an example of application.

However, there are difficulties associated with solubilising cucurbituril, which are known in the prior art. For example, U.S. Pat. No. 6,869,466 describes the use of a solubilising agent to increase the solubility of cucurbituril in aqueous solution. Suitable solubilising agents are described as including metal salts, ammonium salts, acids and polyhydroxylated organic compounds.

WO 2014/077642 describes a composition comprising cucurbit[7]uril which has been solubilised in a buffer and use of the composition in odour removal. Some evidence is provided that odour is complexed with the cucurbituril.

Although cucurbituril host-guest complexes overcome many of the disadvantages associated with cyclodextrin complexes, there is a need for cucurbituril in formulations that provide improved odour control.

SUMMARY OF THE INVENTION

The present invention generally provides a suspension of cucurbituril particles in a medium. The composition may be used for counteracting malodour and has been found to provide superior malodour capture compared to solubilised cucurbituril. The compositions are stable and the cucurbituril particles remain in suspension for a long period of time.

In a first aspect of the invention there is provided a stable suspension composition for counteracting malodour comprising cucurbituril particles suspended in a medium.

In one embodiment the medium is a liquid medium, an emulsion, a wax, an ointment, a gel, a paste, a foam or a liquefied gas.

In a particular embodiment, the medium is a liquid medium. The liquid medium may be polar or non-polar. Examples of polar liquid mediums include aqueous and hydroalcoholic. Non-polar liquid mediums include oil, paraffin, long chain alcohols and fats.

In one embodiment, the composition further comprises a suspending agent. A suspending agent may be required when the medium itself is not capable of suspending the cucurbituril particles. For liquid mediums, suspending agents may be required for compositions comprising cucurbituril particles having a particle size of at least about 0.25 μm or at least about 0.5 μm.

When a suspending agent is present, the compositions of the invention may comprise from about 0.01 to about 25% by weight, in particular from about 0.1 to about 10% by weight, more particularly from about 0.5 to about 5% by weight of suspending agent, based on the total weight of the composition.

In one embodiment, the composition comprises CB[7]. In another embodiment, the composition comprises CB[6]. In certain embodiments, the composition comprises a mixture of different sized cucurbiturils. For example, in one embodiment, the composition comprises CB[6] and CB[7]. In another embodiment, the composition comprises CB[6], CB[7] and CB[8]. In another embodiment, the composition comprises CB[5], CB[6], CB[7] and CB[8].

The cucurbiturils may be present in the composition as a mixture of at least two different sized cucurbiturils selected from CB[5], CB[6], CB[7] and CB[8]. Where the cucurbiturils are referred to as cucurbit[n]uril, the composition comprises a mixture of different sized cucurbit[n]urils, wherein n is an integer from 4 to 20.

In one embodiment, the cucurbituril particles have a particle size from about 0.010 μm to about 50 μm, about 0.1 μm to about 40 μm, about 1 μm to about 20 μm, about 2 μm to about 10 μm, more particularly from about 3 μm to about 5 μm.

In one embodiment, the majority of the cucurbiturils in the composition are uncomplexed.

In a second aspect of the invention there is provided a process for the preparation of a suspension composition according to the first aspect of the invention, comprising the steps of:
a) adding cucurbituril particles to a medium, wherein the medium is in the liquid state; and
b) suspending the cucurbituril particles in the medium under high shear conditions.

Step a) may further comprise the addition of a suspending agent to the medium, wherein the suspending agent may be as described hereinafter.

In a third aspect of the invention there is provided a method of counteracting malodour comprising applying to a source of malodour a suspension composition of the first aspect of the invention.

In a fourth aspect of the invention there is provided use of a suspension composition of the first aspect of the invention for counteracting malodour.

In a fifth aspect of the invention there is provided a method of re-suspending a composition comprising agitation of a composition comprising cucurbituril particles in a medium, to obtain the suspension composition of the first aspect of the invention, whereby agitation re-suspends any particles that may have sedimented.

In a sixth aspect of the invention there is provided a consumer product comprising a suspension composition of the first aspect of the invention.

These and other aspects and embodiments of the invention are described in further detail below.

DETAILED DESCRIPTION OF THE INVENTION

The present inventors have found that stable suspensions of cucurbiturils in various mediums provide improved malodour counteracting properties compared to prior art formulations where the cucurbiturils are solubilised. Without wishing to be bound by any particular theory, it is thought that the solubilisation of cucurbiturils in a solubilising agent such as a buffer, results in complexes being formed with, for example, salts meaning that fewer uncomplexed cucurbiturils are available for binding with malodour. The compositions of the invention have the surprising advantage that a suspending agent, when present, does not interfere with the cavity of the cucurbiturils leaving the cucurbiturils uncomplexed and therefore free for complexation with molecules, for example, malodour molecules.

In particular, suspensions comprising cucurbituril compounds having a distribution of cavity sizes are especially efficient for suppressing malodours consisting of two or more malodour components, even if these components have a low molecular weight, are volatile or have a particularly pungent smell

Cucurbituril

The present invention provides the use of a cucurbituril to form a complex with a malodour molecule.

Cucurbituril is a member of the cavitand family, and the general cucurbituril structure is based on the cyclic arrangement of glycoluril subunits linked by methylene bridges.

The preparation and purification of cucurbituril compounds is well described in the art. For example, Lagona et al. review the synthesis and properties of cucurbituril compounds, including derivatives, analogues and congener within the cucurbituril family.

For example, cucurbit[8]uril (CB[8]; CAS 259886-51-6) is a barrel shaped container molecule which has eight repeat glycoluril units and an internal cavity volume of 479A$^3$ (see structure below). CB[8] is readily synthesised using standard techniques and is available commercially (e.g. Sigma-Aldrich, MO USA).

In one embodiment, the cucurbituril is a CB[5], CB[6], CB[7], CB[8], CB[9], CB[10], CB[11], CB[12], CB[13] or CB[14] compound.

In one embodiment, the cucurbituril is a CB[5], CB[6], CB[7], CB[8], CB[9], CB[10], CB[11] or CB[12] compound.

In one embodiment, the cucurbituril is a CB[5], CB[6], CB[7], or CB[8] compound.

In one embodiment, the cucurbituril is a CB[6] compound.

In one embodiment, the cucurbituril is a CB[7] compound.

In one embodiment, the cucurbituril is a CB[8] compound.

The compositions of the invention may include a single analogue of cucurbituril, or may alternatively include two or more different sized cucurbiturils selected from the group consisting of CB[5], CB[6], CB[7], CB[8], CB[9], CB[10], CB[11], CB[12], CB[13] and CB[14]. A mixture of two or more different cucurbituril is defined as CB[n].

In one embodiment, the cucurbituril is a CB[n] mixture.

When CB[5] is present in the cucurbituril mixture, the concentration of CB[5] may be from about 0.1 to about 99% by weight, more particularly from about 0.5 to about 75% by weight, more particularly from about 1 to about 50% by weight, more particularly from about 2 to about 30% by weight, more particularly from about 5 to about 25% by weight, more particularly from about 10 to about 20% by weight, based on the total weight of the cucurbituril in the composition.

When CB[6] is present in the cucurbituril mixture, the concentration of CB[6] may be from about 0.1 to about 99% by weight, more particularly from about 1 to about 75% by weight, more particularly from about 5 to about 60% by weight, more particularly from about 20 to about 55% by weight, more particularly from about 35% by weight to about 55% by weight, based on the total weight of cucurbituril in the composition.

When CB[7] is present in the cucurbituril mixture, the concentration of CB[7] may be from about 0.1 to 99% by weight, more particularly from about 5 to about 75% by weight, more particularly from about 10 to about 60% by weight, more particularly from about 20% by weight to about 45% by weight, based on the total weight of cucurbituril in the composition. In one embodiment, the concentration of CB[7] is less than 45% by weight, based on the total weight of cucurbituril in the composition.

When CB[8] is present in the cucurbituril mixture, the concentration of CB[8] may be from about 0.1 to 99% by weight, more particularly from about 0.5 to about 75% by weight, more particularly from about 1 to about 30% by weight, more particularly about 5 to about 25% by weight, more particularly from about 10 to about 20% by weight, based on the total weight of cucurbituril in the composition.

When the compositions of the invention comprises at least two different cucurbiturils selected from CB[5], CB[6], CB[7] and CB[8], the total concentration of the CB[5], CB[6], CB[7] and/or CB[8] may be greater than 75% by weight, more particularly greater than about 90% by weight, more particularly greater than about 99% by weight of the total weight of cucurbituril in the composition. The remaining components of the cucurbituril mixture may contain CB[4], CB[9] and/or higher cucurbiturils (i.e. CB[10]-CB[20]), either as a single sized cucurbituril or as a mixture of these sizes.

In a particular embodiment, the cucurbituril mixture comprises between 12 and 17% by weight of CB[5]; 45 and 50% by weight of CB[6]; 22 and 27% by weight of CB[7]; 12 and 17% by weight of CB[8]; and less than 1% by weight of CB[9] and higher cucurbiturils, based on the total weight of cucurbituril in the composition.

The % weights of cucurbiturils described above are based on the total weight of cucurbituril (of all sizes) in the composition.

In other aspects of the invention, cucurbituril derivatives are provided and find use in the methods described herein. A derivative of a cucurbituril is a structure having one, two, three, four or more substituted glycoluril units. A substituted cucurbituril compound may be represented by the structure below:

$$\left[\begin{array}{c} X \\ \Big| \\ N\phantom{xx}N-CH_2 \\ R^2 \diagup\phantom{x}\diagdown R^1 \\ N\phantom{xx}N-CH_2 \\ \Big| \\ X \end{array}\right]_n$$

wherein:

n is an integer between 4 and 20;

and for each glycoluril unit:

each X is O, S or $NR^3$, and

—$R^1$ and —$R^2$ are each independently selected from —H and the following optionally substituted groups: —$R^3$, —OH, —$OR^3$, —COOH, —$COOR^3$, —$NH_2$, —$NHR^3$ and —$N(R^3)_2$ where —$R^3$ is independently selected from $C_{1-20}$alkyl, $C_{6-20}$carboaryl, and $C_{5-20}$heteroaryl, or where —$R^1$ and/or —$R^2$ is —$N(R^3)_2$, both —$R^3$ together form a $C_{5-7}$ heterocyclic ring; or together —$R^1$ and —$R^2$ are $C_{4-6}$alkylene forming a $C_{6-8}$carbocyclic ring together with the uracil frame.

In one embodiment, one of the glycoluril units is a substituted glycoluril unit. Thus, —$R^1$ and —$R^2$ are each independently —H for n−1 of the glycoluril units In one embodiment, n is 5, 6, 7, 8, 9, 10, 11 or 12.

In one embodiment, n is 5, 6, 7 or 8.

In one embodiment, each X is O.

In one embodiment, each X is S.

In one embodiment, $R^1$ and $R^2$ are each independently H.

In one embodiment, for each unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In one embodiment, for one unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In this embodiment, the remaining glycoluril units are such that $R^1$ and $R^2$ are each independently H.

Preferably —$R^3$ is $C_{1-20}$alkyl, most preferably $C_{1-6}$alkyl. The $C_{1-20}$alkyl group may be linear and/or saturated. Each group —$R^3$ may be independently unsubstituted or substituted. Preferred substituents are selected from: —$R^4$, —OH, —SH, —$SR^4$, —COOH, —$COOR^4$, —$NH_2$, —$NHR^4$ and —$N(R^4)_2$, wherein —$R^4$ is selected from $C_{1-20}$alkyl, $C_{6-20}$carboaryl, and $C_{5-20}$heteroaryl. The substituents may be independently selected from —COOH and —$COOR^4$.

In some embodiments, —$R^4$ is not the same as —$R^3$. In some embodiments, —$R^4$ is preferably unsubstituted.

Where —$R^1$ and/or —$R^2$ is —$OR^3$, —$NHR^3$ or —$N(R^3)_2$, then —$R^3$ is preferably $C_{1-6}$alkyl. In some embodiments, —$R^3$ is substituted with a substituent —$OR^4$, —$NHR^4$ or —$N(R^4)_2$. Each —$R^4$ is $C_{1-6}$alkyl and is itself preferably substituted.

In one embodiment, references to a cucurbituril compound are references to variants and derivatives thereof. The cucurbiturils of the invention may be in the native form or they may be modified as described above in order to improve suspendability, and more generally their formulation and handling.

Complex

The compositions described herein comprise an effective, maodour absorbing amount of free uncomplexed cucurbituril. The cucuribturil may be present as single sized cucurbiturils or a mixture of different sized cucurbiturils. In one embodiment, the majority of the cucurbiturils in the composition are uncomplexed, i.e., the cucurbiturils in the composition are substantially free of guest molecules, meaning more than 75% by weight, more particularly more than 90% by weight, still more particularly more than 95% by weight of the cucurbiturils are free of guest molecules, i.e. uncomplexed, based on the total weight of cucurbiturils in the composition. In one embodiment at least 99% of the cucurbiturils are free of guest molecules, based on the total weight of cucurbiturils in the composition. This provides advantages over prior art formulations where the cucurbiturils are solubilised and the amount of uncomplexed cucurbituril will be far less than 75% by weight. When the compositions of the invention come in to contact with malodour molecules, the cucurbiturils form a malodour-cucurbituril complex which results in malodour suppression.

When forming a complex with a cucurbituril, the malodour molecule is physically bound to the cucurbituril substrate. The terms "physically bound", "physical bonding" and "physical linkage" include bonding by Van der Waals forces and other types of physical bond. In the present context, hydrogen bonds are also considered as physical bonds. Systems that are capable of establishing strong physical bonding with malodour have considerable advantages over systems relying on covalent (chemical) bonding.

In particular, physical binding allows the formation of complexes with a multitude of malodours having a multitude of chemical structures and functions. Even malodour molecules that have no reactive groups can bind physically to the cucurbiturils.

The cucurbituril-malodour complex may be a binary or ternary complex. Thus, the cucurbituril may hold one (binary) or two (ternary) guest malodour molecules within its cavity. Where a cucurbituril holds two malodour molecules, the malodour molecules may be the same or they may be different. A cucurbituril that is capable of hosting two malodour molecules may also be capable of forming a stable binary complex with a single malodour. The formation of a ternary guest-host complex is believed to proceed via an intermediate binary complex.

In one embodiment, the cucurbituril is capable of forming a ternary complex. For example, CB[8] is capable of forming a ternary complex.

In one embodiment, the cucurbituril is capable of forming a binary complex. CB[8] may also form a binary complex.

In one embodiment, the cucurbituril is capable of forming ternary and binary complexes. For example, CB[8] is capable of forming a ternary or a binary complex, depending upon the nature of the guest.

The binding constant K for a binary complex between a malodour M and a cucurbituril CB[x], where x is an integer, is defined according to the Le Chatelier principle of mass action as:

$$M + CB[x] \leftrightarrows MCB[x]$$

$$K = [MCB[x]]/([M]*[CB[x]])$$

where the square brackets denote the concentration of the species in mol/L.

The applicant has established that to perform as a malodour counteracting system, a malodour-cucurbituril complex must have a binding constant preferably larger than 100 $M^{-1}$. In one embodiment, the binding constant is at least 1000 $M^{-1}$.

In certain embodiments, the compositions of the invention comprise cucurbituril complexed with a fragrance molecule. When the composition is exposed to a source of malodour, the complexation of the malodour with the cucurbituril triggers the release of the fragrance molecule. In one embodiment, there is therefore provided pro-fragrance suspension compositions comprising particles of cucurbituril-fragrance complexes suspended in a medium. Suitable fragrance molecules are described in GB 16 02664.3, which is hereby incorporated by reference.

Malodours

The term "malodour" refers to unpleasant odours which are frequently encountered in everyday life and have a variety of origins. Typical malodours include odours that emanate from uncontrolled industrial activity, from human and pet body such as perspiration and excretion, from kitchen and food processing, from tobacco smoke, and from mould. Some of the most disturbing malodour for the human being are human or animal sweat, faeces, and urine; wet pet; food and cooking odours, especially garlic, cabbage, fish and onion; and the like. Malodours may also emanate from the fatty acid and fatty acid derivatives present in consumer products, for example in soaps, detergents, shampoos, and conditioners. Other examples of particularly undesirable malodours are those produced by depilatory creams, hair dyes and hair relaxers (sulphur compounds). All of these malodours are particularly pungent.

Cucurbituril may be used to counteract a broad range of malodour molecules.

In the context of the present invention, the term "malodour counteraction" or "malodour counteracting" is considered as equivalent to "malodour suppression", "malodour mitigation" or "malodour neutralisation". The result is a significant decrease of the intensity of the malodour perception by any person exposed to the source of the malodour. The intensity of odours is generally measured by using the Labelled Magnitude Scale (LMS), a definition of which can be found in Green B G, Shaffer G S and Gilmore M M 1993, Derivation and evaluation of a semantic scale of oral sensation magnitude with apparent ratio properties, Chemical Senses. 18(6):683-702. For odours, the scale encompasses the following strength attributes: Barely Detectable, Weak, Moderate, Strong, Very Strong and Strongest Imaginable. In the context of the present invention, a "significant decrease" means that the intensity attribute of the malodour, after application of the cucurbiturils, is Weak or Barely Detectable.

Alternatively, a linear scale may be used, extending for example from 0 (no intensity perceived) to 10 (highest intensity perceived).

Odour intensity scores are preferably obtained by a panel of several people.

In one embodiment, the malodour to be counteracted is a complex malodour, comprising more than one malodour component.

In one embodiment, the complex malodour comprises malodour components having a diversity of chemical functions.

CB[5] having a cavity volume of 82 Angström$^3$, preferably binds small gaseous malodours, such as acetylene, hydrogen sulphide and carbon disulphide.

Larger malodour molecules comprising O-, N- and S-heteroatoms preferably bind to larger cucurbiturils (e.g. CB[7] and CB[8]).

In one embodiment, the malodour molecule is a nitrogen-containing molecule, a sulphur-containing molecule or an oxygen-containing molecule.

The malodour may be selected from, but not limited to:

Nitrogen- and sulphur-containing molecules, such as Allyl amine; Methyl amine; Ethyl amine; Cyclobutyl amine (cyclobutanamine, urine), Cyclopentyl amine (cyclopentanamine); Cyclohexyl amine (cyclohexanamine); Cycloheptyl amine (cyclobutanamine); Isopropylamine; Butylamine; Dibu-tylamine (N-Butyl-1-butanamin); Dimethyl ethanolamine (2-(Dimethylamino)ethanol); Methyl ethanolamine (2-(Methylamino)ethanol); Diethyl ethanolamine (2-(Diethylamino)ethanol); Diethylamine (N-methyl-ethanamine, fishy); Dipropyl amine (N-Propyl-1-propanamine); Diiso-propylamine (N-Isopropyl-2-propanamine); Dimethyl acetamide (N,N-Dimethylacetamide); Ethyl methylamine (N-Methylethanamine); Ethyl propylamine (N-ethylpropanamide); Trimethyl amine (fishy); Triethylamine (fishy); Ethylene diamine (1,2-ethanediamine, musty ammoniacal); Propylene diamine (1,3-propanediamine); tetramethylenediamine (1,4-butanediamine, Putrescine, foul); Ethylene imine (Aziridine, ammoniacal); Morpholine (fishy); Ethyl morpholine (4-ethylmorpholine, sour); Pyrrolidine (semen); Methyl ethyl pyridine (2-Ethyl-3-methylpyridine); Pyridine (burnt, sickening); Vinyl pyridine (4-vinylpyridie, nauseating); Skatole (3-methylindole, faecal); Indole (faecal); Cadaverine (Pentane-1,5-diamine, putrid); Hydrogen sulphide (rotten egg); Allyl disulphide (3-(Allyldisulfanyl)-1-propene, garlic); Ethyl isothiocyanate (isothiocyanatoethane; pungent, mustard, garlic); Ally isothiocyanate (3-isothiocyanatoprop-1-ène, sulphurous); Allyl mercaptan (2-Propene-1-thiol, garlic, sulphurous); Allyl sulphide (3-(Allylsulfanyl)-1-propene; sulphurous); Diallyl sulphide (3-(Allylsulfanyl)-1-propene; sulphurous); Dimethyl disulphide ((methylsulfanyl)ethane, unpleasant, garlic); Dimethyl trisulphide (Dimethyltrisulfane, foul); Diethyl sulphide ((Ethylsulfanyl)ethane, sulphurous); Butyl sulphide (1-(Butylsulfanyl)butane, garlic, violet); Diethyl trisulfide (Diethyltrisulfane, foul, garlic); Ethyl methyl disulphide ((methylsulfanyl)ethane, sulphurous); Phenyl sulphide (1,1'-sulfanediyldibenzene, sulphurous); Ethyl mercaptan (1.ethanethiol, sulphurous); Amyl mercaptan (1-Pentanethiol); Isoamyl mercaptan (3-methylbutane-1-thiol; sulphurous, oinion); Butyl mercaptan (1-Butanethiol, skunk-like); Isobutyl mercaptan (2-methylpropane-1-thiol, sulphurous, mustard); Dodecyl mercaptan (1-dodecanethiol); Carbon disulphide (Methanedithione, disagreeable, sweetish); Dimethyl trithiocarbonate (Dimethyl carbonotrithioate); Thiophenol mercaptan;

Oxygen-containing five-member ring molecules, such as Sotolone; nor-Sotolone;

Saturated and unsaturated alkyl and hydroxyalkyl carboxylic acids, such as Acetic acid, Propionic acid, Butyric acid, iso-Valeric acid, n-Valeric acid, 2-Methyl-butyric acid, 3-Methyl-2-hexenoic acid, and 3-Methyl-3-hydroxy hexanoic acid.

Suspension Medium

The compositions of the present invention comprise cucurbituril particles which are suspended in a medium.

The suspension medium may be selected from the group consisting of liquid medium, emulsion, wax, ointment, gel, paste, foam or a liquefied gas.

In one embodiment the medium is a liquid medium. The liquid medium may be polar (for example aqueous or hydroalcoholic), or non-polar (for example an oil, a paraffin, a long chain alcohol, or a fat).

In particular, the liquid medium may be selected from the group consisting of water, ethanol, n-propanol; tert-butanol; 2-methoxyethanol; 2-ethoxyethanol; 3-methoxy-3-methyl-1-butanol; isopropanol; isbutanol; 1,2-propanediol; 1,3-propanediol; 1,2-butanediol; 1,2-pentanediol; 1,2-hexanediol; 1,2-heptanediol; 1,3-butanediol; 1,4,-butanediol; 3-methyl-1,3-butanediol; 1,4-butylene glycol; 2,3-butylene glycol; trimethylene glycol; tripropylene glycol; propylene glycol; dipropylene glycol; ethylene glycol; diethylene glycol; hexylene glycol (2-Methyl-2,4-pentanediol); mono and polyalkylene glycols and ethers and esters thereof, such as propylene glycol methyl ether, dipropylene glycol methyl ether, tripopylene glycol methyl ether, propylene glycol methyl ether acetate, dipropylene glycol methyl ether acetate, propylene glycol n-propyl ether, dipropylene glycol n-propyl ether, propylene glycol n-butyl ether, dipropylene glycol n-butyl ether, tripropylene glycol n-butyl ether, propylene glycol phenyl ether, propylene glycol diacetate, dipropylene glycol dimethyl ether, diethylene glycol ethyl ether, diethylene glycol methyl ether, diethylene glycol n-butyl ether, diethylene glycol hexyl ether, diethylene glycol n-butyl ether acetate, ethylene glycol propyl ether, ethylene glycol n-butyl ether, ethylene glycol hexyl ether, ethylene glycol n-butyl ether acetate, triethylene glycol methyl ether, triethylene glycol ethyl ether, triethylene glycol n-butyl ether, ethylene glycol phenyl ether, ethylene glycol n-butyl ether; isosorbide mono- and di-ethers and esters, such as dimethyl isosorbide; glycerin; glycerin carbonate; 2,3-ortho isopropyliden glycerin; (2,2-Dimethyl-1,3-dioxolan-4-yl)methanol; alkyl lactates; alkyl lactamides; alkyl cabonates, PEG-4 (PEG-4 is also known as PEG-200); PEG-8 (PEG-8 is also known as PEG-400); PPG-14 butylether; syntethically or plant derived hydrocarbons; mineral oils; paraffins, isoparaffins, glyceride esters, such alkyl triglycerides (for example coconut oil, sunflower oil, and the like); silicones (for example dimethicone, and the like) or a mixture thereof.

In one embodiment, the liquid medium is selected from water, ethanol, methanol, isopropanol or a mixture thereof. In one embodiment, the liquid medium is water.

In one embodiment, the medium is an emulsion, a nanoemulsion, a microemulsion or a foam. The emulsion or nanoemulsion may be an oil-in-water emulsion, a water-in-oil emulsion or a multiple emulsion. The microemulsion may be an oil-in-water emulsion, a water-in-oil emulsion or a co-continuous microemulsion.

When the medium is an emulsion or microemulsion, the cucurbituril particles may be located in one or both of the immiscible liquid phases, or adsorbed at the water/oil interface. Often a surfactant is required to stabilise the emulsion. Suitable surfactants are known to the skilled person. When present the surfactant forms a phase in the emulsion which may be structured. For example the surfactant may form liquid crystalline phases, lamellar phases, cubic phases, hexagonal phases, liposomes, vesicles and the like. Such surfactant phases may have a melting temperature higher than room temperature.

When the medium is a foam, the cucurbituril particles may be located in the liquid continuous phase or adsorbed at the liquid/air interface.

In one embodiment the medium is wax. The wax may be a hard wax, a soft wax or a fat synthetically or naturally derived. The wax may consist of hydrocarbons or esters of fatty acids such as beeswax, candelilla wax, carnauba wax, microcrystalline wax, ozokerite wax, paraffin wax, ceresine wax, soy wax. The cucurbituril particles are added and suspended in the wax at a temperature above the wax melting point and then the melted wax is cooled down to room temperature.

In another embodiment, the medium is an ointment. The ointment comprises an ointment base. The ointment base may be selected from the group consisting of a hydrocarbon base, an absorption base, a water-soluble base, an emulsifying base or a vegetable oil.

In yet another embodiment, the medium is a gel or paste made using rheology modifiers such as linear or cross-linked acrylic acid copolymers, linear or cross-linked methacrylic acid copolymers, polyvinyl alcohol, polyvinyl pyrrolidone, polyoxyalkylene, block-copolymers such as poly(ethylene oxide-b-propylene oxide), poly(oxyethylene-b-di methylsiloxane) copolymers, and poly(oxyethylene-graft-di methylsiloxane) copolymers, hydrophobic ethoxylated polyurethanes, polyether urea polyurethanes, polyether polyols, starch, water soluble polysaccharides or modified polysaccharides, such as modified starch, gums, alginates, clays, pectins, and the like, modified celluloses, gelatine, or a mixture thereof.

In yet another embodiment, the medium is a liquefied gas such as methane, ethane, propane, n-butane, isobutene, n-pentane, isopentane, dimethyl ether, methyl ether, Dymel propellants, or a mixture thereof.

The medium may comprise a suspending agent to help suspend the cucurbituril particles in the medium to form a suspension. A suspending agent is required when the medium is not itself able to suspend the cucurbituril particles.

For liquid mediums, a suspending agent may be required when the average particle size of cucurbiturils is greater than about 0.5 µm, or greater than about 0.25 µm and the medium is a liquid. It will be understood by the skilled person that this threshold may vary by about ±0.2 µm, for example ±0.1 µm or ±0.05 µm. Above this threshold, the suspending agent assists in the dispersal of the cucurbituril particles to provide a stable suspension. Below a particle size of about 0.25 to about 0.5 µm colloid self-stabilisation of the particles means that no suspending agent is required to maintain the particles in suspension. This is due to non-aggregating particles, i.e. particles which have no affinity for one another or the affinity is compensated by electrostatic repulsions.

When present, the suspending agent may be solubilised in the medium or the suspending agent may itself be suspended as a suspension in the medium, for example clay is a suspending agent which may form a suspension in a liquid medium.

The suspending agent may be selected from the group consisting of cross-polymers, also known as Carbomers or Carbopol®, such as acrylic acid cross-polymers, methacrylic acid cross-polymers, acrylic acic-co-methacrylic acid cross copolymers, and cross-linked polymers of acrylic and/or methacrylic acid with alkyl (meth)acrylates; styrene (meth)acrylate copolymers, vinyl acetate (meth)acrylate copolymers, polyvinylpyrrolidone dimethylaminoethyl (meth)acrylate copolymers, and methacryloyl betaine (meth)acrylate copolymers, vinyl ether maleic anhydride, and the like. These cross-polymers and copolymers may be used in their native form or partially neutralized with alkali metals, such as sodium or ammonium. The cross-polymers are typically cross-linked with sucrose allyl ethers, pentaerythritol allyl ether, propylene glycol allyl ethers, and the like, or a mixture thereof.

The suspending agent may also be selected from the group selected from polyvinyl alcohol; polyvinyl pyrrolidone; sodium polystyrene sulphonate; styrene acrylate copolymers and their salts; block and graft copolymers having hydrophobic blocks and hydrophilic blocks, such as poly(oxythylene-b-oxyproylene) block copolymers and poly(oxyethylene-b-di methylsiloxane) block and graft copolymers; hydrophobic ethoxylated polyurethanes; gum Arabicum; gum tragacanthe; gum acacia; gum xanthan; locust bean gum; gellan gum; alginates; carrageenan; agar; modified cellulose, such as methyl cellulose, carboxymethyl cellulose sodium carboxymethylcellulose, hydroxyethyl cellulose, hydroxypropyl cellulose, hydroxypropylmethyl cellulose; microcrystalline cellulose; starch alkenyl succinates; starch; vegetal fibers; pectins; gelatin; clays, such as bentonites and montmorillonites; and the like; or a mixture thereof.

In one embodiment, the suspending agent is selected from the group consisting of native or partially neutralized acrylic acid cross-polymers, methacrylic acid cross-polymers, acrylic acid-co-methacrylic acid copolymers, acrylic acic-co-methacrylic acid cross copolymers, cross-linked polymers of acrylic and/or methacrylic acid with alkyl (meth)acrylates, styrene (meth)acrylate copolymers, polyvinylpyrrolidone di methylaminoethyl (meth)acrylate copolymers, and methacryloyl betaine acrylate copolymers, vinyl ether maleic anhydride copolymers; polyvinyl alcohol, polyvinyl pyrrolidone, sodium polystyrene sulphonate; block and graft copolymers having hydrophobic blocks and hydrophilic blocks; hydrophobic ethoxylated polyurethanes; gum Arabicum; gum tragacanthe; gum acacia; gum xanthan; locust bean gum; gellan gum; alginates; carrageenan; agar; modified cellulose, such as methyl cellulose, carboxymethyl cellulose, sodium carboxymethylcellulose, hydroxyethyl cellulose, hydroxypropyl cellulose, hydroxypropylmethyl cellulose; microcrystalline cellulose; starch alkenyl succinates; starch; vegetal fibers; pectins; gelatin; clays, such as bentonites and montmorillonites; and mixture thereof.

In one embodiment, the suspending agent is an acrylic acid cross-polymer or xanthan gum. In particular, the suspending agent may be cross-linked polyacrylic acid cross-polymers or xanthan gum.

In some embodiments, the compositions of the invention may further comprise a surfactant or emulsifier, in addition to a suspending agent. It will be appreciated by the skilled person that in certain instances, a surfactant or emulsifier may be used instead of a suspending agent. The surfactant or emulsifier may be selected from anionic surfactants; cationic surfactants; cationogene surfactants; zwitterionic surfactants; amphoteric surfactants; non-ionic surfactants.

Suspending agents substantially increase the viscosity of the medium at low shear, even to the extent that the suspension has a shear-dependent gel state (also called "yield region") and may be characterised by a "yield stress". Below a certain shear value, the suspension behaves as a soft elastic material and has the capability of maintaining the cucurbituril particles of the invention in suspension. The materials are pseudoplastic and on shearing above the yield value, the suspension flows and the materials may be handled by pouring.

Particularly interesting for the sake of the present invention are suspending agents providing, in the yield region of the suspension, a storage modulus from about 100 to about 250 Pa and a loss modulus which is preferably lower than the storage modulus. For example, from about 10 to about 90 Pa, at strain between about 0.01 and 0.1% and a temperature of 20 degrees centigrade, as measured by rheology under strain sweep measurement conditions (see for example http://www.tainstruments.com/pdf/literature/AAN016_V1_U_StructFluids.pdf, consulted Aug. 22, 2016, and N. Koumakis, P. Ballesta, R. Besseling, W. C. K. Poon, J. F. Brady, and G. Petekidis, AIP Conference Proceedings 1518, 365 (2013)).

In one embodiment, the composition comprises from 0.01 to 25% by weight, in particular from 0.05 to 10% by weight, more particularly from 0.1 to 5% by weight of suspending agent, based on the total weight of the composition. In embodiments where the medium is a liquid medium, the composition may comprise from 0.01 to 10% by weight, in particular 0.1 to 5%, more particularly 0.1 to 1% by weight of suspending agent, based on the total weight of the composition.

In another embodiment, where the medium is an aqueous liquid medium, the suspension is formed of cucurbiturils having a particle size below about 0.5 µm, in particular below about 0.25 µm, wherein the suspension is stabilised by electrostatic repulsive interactions and is substantially free of suspending agents. For example, the cucurbituril compounds may have a zeta potential below −10 mV or above +10 mV.

The zeta potential of a particle is the electrostatic potential on the surface separating the region of the particle where the electrostatic charges are bound from the region around the particles where the electrostatic charges are diffused. Such a potential can be measured and interpreted in terms of colloidal stability can be found in "Zeta Potential in Colloid Sciences" (Robert. J. Hunter; Academic Press, London 1988).

In one embodiment, the composition comprises from 0.1 to 5% by weight, more particularly from 0.2 to 3% by weight, even more particularly from 0.5 to 1.5% by weight of cucurbituril particles based on the total weight of the composition. However, the skilled person will appreciate that in certain instances the concentration of cucurbituril particles may be higher, for example up to 50 or up to 60% by weight or possibly more. Therefore in certain embodiments, the composition comprises 0.1 to 60% by weight, for example from 0.1 to 50% by weight, for example from 0.1 to 20% by weight, for example 0.1 to 10% by weight, for example from 0.1 to 5% by weight, more particularly from 0.2 to 3% by weight, even more particularly from 0.5 to 1.5% by weight of cucurbituril particles based on the total weight of the composition.

Malodour Counteracting Compositions

The cucurbituril particles in the compositions of the present invention may have a particle size from about 0.010 µm to about 50 µm, in particular from about 0.1 µm to about 40 µm, more particularly from about 1 µm to about 20 µm, more particularly from about 2 µm to about 10 µm, even more particularly from about 3 µm to about 5 µm. In one embodiment, the particle size is between about 3 µm and 5 µm.

Particle size refers to the average diameter of the particle. Methods for determining particle size are known in the art. One such method is microscopical examination which involves using microscope pictures to measure particle size. A broad range of microscopes may be used, such as optical light microscope, electron microscope, or atomic force microscopy. Microscopical examination usually provides a number-averaged particle size and therefore, in one embodiment, the number-averaged particle size of the cucurbituril particles is between about 0.01 µm and about 50 µm, between about 0.1 µm and 40 µm, between 1 µm and about 20 µm, more particularly between about 2 µm and about 10 µm, more particularly between about 3 and about 5 µm. The size of particles between 1 µm and about 20 µm may be determined by optical light microscopy.

In one embodiment, the compositions of the invention have a viscosity (at 20 degrees centigrade) of
a) between about 400 and about 1500 mPas, more particularly between about 800 and about 1000 mPas at shear rates of about 2 s$^{-1}$; and
b) between about 10 and about 500 mPas, more particularly between about 50 and about 300 mPas at a shear rate between about 30 s$^{-1}$ and about 100 s$^{-1}$; and
c) between about 0.5 and about 5 mPas, more particularly between about 0.8 and about 2 mPas at a shear rate higher than 1000 s$^{-1}$.

The viscosity and the shear rate dependence of the viscosity of a suspension according to the invention may be performed by any known means, for example, by using a capillary viscometer, a rotatory disc viscometer, or a rheometer, at the different shear rates specified herein above. These measurements may for example be performed by using rheometers that are commercially available from Malvern Instruments Ltd, TA Instruments, or Brookfield Ametek Inc. An introduction to the rheology of suspensions may be found, for example, in TA Instruments technical literature reference AAN016 "Understanding Rheology of Structured Fluids", available under http://www.tainstruments.com/pdf/literature/AAN016_V1_U_StructFluids.pdf, consulted Aug. 12, 2016.

It will be understood by the person skilled in the art, that the above viscosity values may be adapted depending on the application. Methods for altering the viscosity of a composition are known in the art. For example, for spray application, the desired viscosity is dependent on the type of spray nozzle and/or spraying technology used, and on the desired spray pattern, and can be adjusting by altering the amount of suspending agent in the composition.

The compositions of the invention may also include one or more additives known to those skilled in the art.

In one embodiment, the compositions described herein further comprise one or more additives selected from the group consisting of surfactants, biocides, viscosifying agents, antioxidants, chelating agents, wetting agents, deposition agents, foam control agents, fragrances, solvents, dyes, pigments, antiperspirant, and conditioning agents.

In one aspect of the present invention, there is provided a method of counteracting malodour comprising applying to a source of malodour a suspension composition of the invention.

In another aspect of the present invention, there is provided use of a suspension composition as defined herein for counteracting malodour.

The suspension compositions of the invention may also be used to provide malodour counteracting properties to textiles, to functional textiles and to textile finishing products; to air and various materials, such as paper, wood, plastics, stone, ceramics, metals, metal wool, wool, fibres, foams, filter material, absorbents, adsorbents, plasters, paints, inks, and the like.

In particular, the suspension compositions of the invention may be used to provide malodour counteracting properties to diapers, incontinency pads, feminine hygiene products, sanitary napkins, shoe soles, denture bath and wound dressings, as well as pet litters, chemical toilets, and the like.

The composition described herein may also be admixed with or incorporated into a perfume oil, before addition to a product.

If the composition of the invention is added to a perfume oil, the resulting mixture may then be microencapsulated by any methods known to the art, such as by spray drying, spray granulation, matrix particle formation, core-shell encapsulation, and the like.

In one embodiment, the compositions of the invention are applied to the source of malodour by spraying.

In one aspect of the invention, there is provided a consumer product comprising a suspension composition of the present invention. The consumer product may be for laundry care, home care, personal care or pet care. For example the consumer product may be a pet care product, toilet cleaner, fabric care product, a detergent, a cleansing composition, a shampoo, a softener, a softener sheet, a conditioner, a refresher, an air freshener, a deodorizing composition, a personal deodorant, an antiperspirant, a cosmetic product, a fine fragrance, a body mist, a candle, a hard surface cleaner, a cleansing wipe or mop, a soap, a styling gel, a humidity absorber, an air filtration device, a finishing product, a diaper or sanitary product, such as incontinency pads, feminine hygiene products, sanitary napkins, shoe soles, denture bath and wound dressings, as well as pet litters, chemical toilets, and the like.

The consumer product may be in the form of powders or granulates, tablets or single dose units, wipes or sponges, compressed gas, aerosols or liquid dispensers, creams, balsam, polish, waxes, and the like.

In one embodiment, the consumer product is a device selected from a spray device (e.g. finger spray) or an atomizer (e.g. using venturi or piezoelectric nozzles).

The composition may be applied to an inanimate surface, for example, a kitchen or bathroom surface.

In one embodiment, the inanimate surface is a granule or bead. In particular, the compositions described herein may be applied to a granulated material having an average particle size between 0.1 and 10 millimetres, more particularly between 0.5 and 5 millimetres. The granulated material can be composed of granules having irregular shape or granules having regular shape, such as spherical beads. The composition may be applied by spraying or by blending the granulated material with the suspension according to the invention. The application can be performed directly to a bed of granulated material, for example on a still bed, a moving bed or a fluidized bed, by any of the methods known to the art, such as spray coating, drum coating, or the like.

In one embodiment, the pH of the composition is from about 2.0 to 12.0, for example from about 4.0 to about 9.0, more particularly from about 5.0 to about 7.5. In one embodiment, the pH is from 5.5 to 6.5, in particular pH 5.5. It will be understood by the skilled person that the pH of the composition will be dependent on its application and the suspending agent used and that the pH can be adjusted accordingly.

Another advantage of the present invention is that the pH of the composition remains substantially unchanged over a prolonged period of time. Substantially unchanged means that there may only be a variance of ±0.5, preferably ±0.3, in pH over a period of at least one day, at least one week, at least one month, at least three months or at least one year. Preferably, the pH remains substantially unchanged for at least three months. The compositions of the invention are therefore particularly suitable for commercial products which generally require stability for 90 days at 40° C.

Process for Preparation of Compositions

In an aspect of the invention, there is provided a process for the preparation of the suspensions described herein, comprising the steps of:
a) adding cucurbituril particles to a medium, wherein the medium is in the liquid state;
b) suspending the cucurbituril particles in the medium under high shear conditions.

Suitable methods for achieving high shear conditions are ultrasonication and high pressure homogenisation. Other suitable methods are known in the art.

In one embodiment, step a) further comprises adding a suspending agent to the medium. The suspending agent is as described herein.

In one embodiment, steps a) and b) are performed at a temperature higher than the melting point of the medium and the composition is then cooled to room temperature to form a wax or a paste.

In one embodiment, the medium comprises a gelling agent in the sol state, and the medium is allowed to form a gel, by any means known in the art, such as by cooling, settling, and/or cross-linking.

In one embodiment, gelation is provoked by changing the pH of the medium.

In one embodiment, step b) is performed by using a high shear mixer, such as a rotor-stator high shear mixer, or a high pressure homogenizer.

Stable Suspensions

Suspension stability is the ability of a suspension to remain in its original state. A "stable suspension" is a well-known term in the art and will be understood by the skilled person to mean a homogenous suspension of a solid in a liquid. In some embodiments, the mediums described herein have a melting point higher than room temperature. In such embodiments, a stable suspension is understood to mean a homogenous suspension of a solid in a liquid, wherein the liquid may then be cooled to room temperature to form a solid or semi-solid.

In one embodiment, the cucurbituril particles remain homogeneously suspended throughout the medium for at least one day, at least one week, at least one month, at least three months or at least one year when stored at a temperature from 4° C. to 50° C. It is preferred that the suspension is stable for at least three months when stored at a temperature from 4° C. to 50° C.

In one embodiment, at least 80%, at least 85%, at least 90%, at least 95% or at least 99% of the cucurbituril particles are suspended. In one embodiment, 100% of the cucurbituril particles are suspended. The percentage of cucurbituril particles in suspension can be determined by measuring the turbidity of the suspension by turbidimetry or by nephelometry. The measurement is based on the fact that the particles in suspension scatter the light, which results in a decrease of light transmission through the sample. Within a certain range of particle number in the sample, also referred to as linear domain, the turbidity is proportional to the number of particles in the sample. In this domain, comparison with samples having known particle number allows a suitable estimate of the percentage of particles in the sample. If the sample is too concentrated to be in the linear domain, then it is diluted accordingly with particle-free suspending medium. In nephelometry the intensity of the scattered light is measured, while, in turbidmetry, the intensity of light transmitted through the sample is measured. Commercial turbidity measuring instruments can for example be purchased from Hach Company, US, or from ThermoFischer Scientific Company, Switzerland.

The evolution of a suspension of cucurbituril particles over time is a suitable method to evaluate the stability of this suspension. This evolution may be monitored by measuring over time the turbidity along the vertical axis of a sample, for example by scanning up and down a sample in a glass tube over time. Instruments that perform this kind of measurements are known under the name Turbiscan, available from Formulaction SA, France.

In one embodiment, the cucurbituril particles of the present invention are suspended in a solid wax or a permanent, strong, chemically cross-linked gel, thereby forming a suspension that is stable over a long period of time, for example more than 1 month, more than 3 months or more than 1 year.

In one embodiment, the cucurbituril particles of the present invention are suspended in a liquid medium optionally comprising a suspending agent, as defined hereinabove.

The cucurbituril particles in the compositions of the present invention, when suspended in a liquid medium or a weak physically cross-linked gel, may settle over time forming sediment in the medium. The compositions of the invention are well-stabilised and so a settled system will re-suspend readily with agitation. A settled system can be identified by visual separation. When the cucurbituril particles are fully suspended, the suspension appears translucent or opaque.

Hence, one aspect of the invention there is provided a method for re-suspending a composition comprising cucurbituril particles in a medium by agitation, such as by mechanical or manual stabilisation whereby agitation re-suspends any particle sedimentation.

In one embodiment, the stabilisation is by mechanical stirring, manual stirring, mechanical shaking, manual shaking or heating.

Certain aspects and embodiments of the invention will now be illustrated by way of example and with reference to the figures described above.

EXPERIMENTAL AND RESULTS

Example 1: CB[n] Suspensions in Water with Polyacrylic Acid (PAA) (Suspending Agent)

1.1 CB[n] Suspension Formulations

Stable CB[n] suspensions were formulated in polyacrylic acid (PAA) cross-polymer gels. Compositions with various pH and PAA concentrations were formulated. The CB[n] mixture was made up of 15% by weight of CB[5], 48% by weight of CB[6], 25% by weight of CB[7] and 12% by weight of CB[8], based on the total amount of cucurbituril.

Formulation procedure: A 1% weight PAA (Carbopol™ 940) stock solution was prepared by adding the PAA to water whilst mixing with an overhead stirrer. In a separate vessel, CB[n] was added to water to a 2% weight concentration, the mixture was then added to the PAA solution at 1:1 ratio for a system with PAA and CB[n] final concentrations of 0.5 and 1% respectively by weight. The CB[n] concentration was kept constant at 1% weight and the PAA was further diluted to obtain samples with a series of PAA concentrations, based on the total weight of the composition. The PAA/CB[n] mixtures were stirred with a Silverson homogenizer (Model L5M) at 5000 rpm for 5 minutes. The pH was then adjusted with NaOH (7M solution) to the desired pH. The mixture was then further stirred with the homogenizer for 10 minutes at 5000 rpm. The result was a sprayable translucent homogenous suspension of CB[n].

TABLE 1

1% weight CB[n] suspensions in PAA gels

| PAA concentration % weight | pH | Observations (sedimentation at 37° C.) |
|---|---|---|
| 0.35 | 5.50 | No sedimentation within 90 days |
| 0.40 | 5.50 | No sedimentation within 90 days |
| 0.45 | 5.50 | No sedimentation within 90 days |
| 0.50 | 5.50 | No sedimentation within 90 days |

TABLE 2

1% weight CB[n] suspensions in PAA systems of different pH

| PAA concentration % weight | pH | Observations (sedimentation at 37° C.) |
|---|---|---|
| 0.35 | 5.50 | No sedimentation within 90 days |
| 0.35 | 6.00 | No sedimentation within 90 days |
| 0.35 | 6.50 | No sedimentation within 90 days |

It is apparent from the visual observations that CB[n] can be successfully suspended in PAA gels.

1.2 pH Stability of CB[n]/PAA Suspensions

The pH of CB[n]/PAA suspensions kept at 37° C. was monitored for 28 days. Table 1 shows the pH of compositions listed in section 1.1.

TABLE 3 pH of CB[n]/PAA suspensions initially and after 7, 14, 21 and 28 days.

| PAA concentration % weight | Initial pH | 7 days | 14 days | 21 days | 28 days |
|---|---|---|---|---|---|
| 0.35 | 5.50 | 5.46 | 5.41 | 5.51 | 5.41 |
| 0.40 | 5.50 | 5.52 | 5.54 | 5.44 | 5.52 |
| 0.45 | 5.50 | 5.55 | 5.59 | 5.52 | 5.56 |
| 0.50 | 5.50 | 5.54 | 5.52 | 5.52 | 5.49 |
| 0.35 | 6.00 | 5.99 | 5.93 | 5.99 | 5.87 |
| 0.35 | 6.50 | 6.49 | 6.46 | 6.48 | 6.36 |

Table 3 shows no significant changes in pH of all compositions indicating suspension stability.

1.3 Sprayability of CB[n]/PAA Suspensions

To determine the applicability of CB[n]/PAA compositions in sprayable systems, particle size and rheology measurements were conducted.

Figure 1:
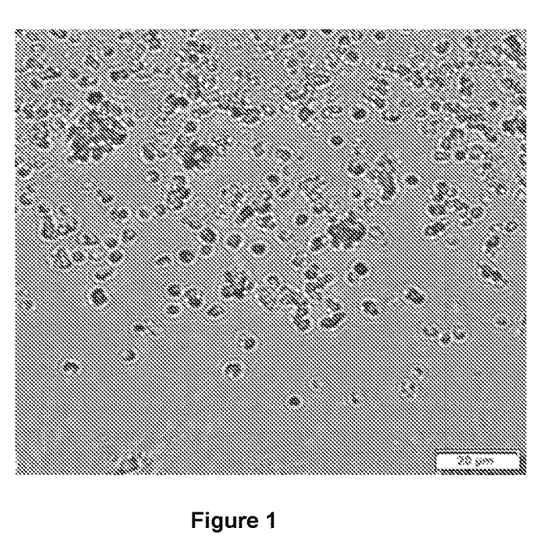
FIG. 1 shows a micrograph of CB[n] particles suspended in water containing polyacrylic acid as suspending agent, obtained by optical microscopy. Comparison with the scale on the micrograph shows that the particle size of the CB[n] particles is about 3 to 5 micrometres.

Particle size: optical microscopy is used to determine the size of CB[n] particles in suspension. The CB[n] particles range from 1 to 20 µm with the majority of particles having a size below 5 µm (FIG. 1) which makes the CB[n] suspensions suitable for sprayable systems.

Rheology measurements: The key measurements were of two types, both involving an increase followed by a decrease in shear. The first type was in steady, i.e. continuous, shear rate. Viscosity was measured at 10 logarithmically spaced intervals per decade in shear rate over the range from 0.1 s$^{-1}$ to 100 (or 500) and back to 0.1 s$^{-1}$ at a temperature of 20 degrees centigrade. The maximum time at each rate was 2 minutes. The second measurement type was in oscillatory shear at a frequency of 1 Hz and the oscillatory amplitude was first increased and then decreased at 20 logarithmically spaced increments per decade of the shear stress. The minimum stress was set such that the material response was in the linear viscoelastic regime (i.e. the measured parameters were independent of shear, where strain was typically <1%) and the maximum stress was set to a point significantly after yielding (strain typically >100%).

Figure 2:
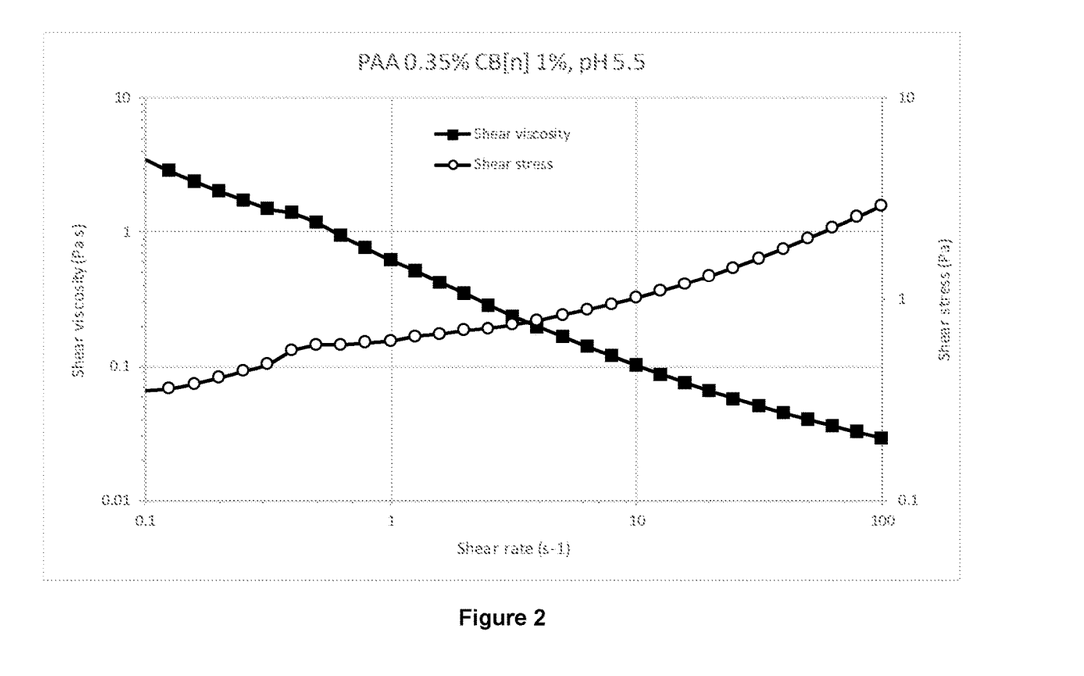
FIG. 2 shows the shear velocity and shear stress of a CB[n]/polyacrylic acid suspension in water as a function of shear rate.
Figure 3:
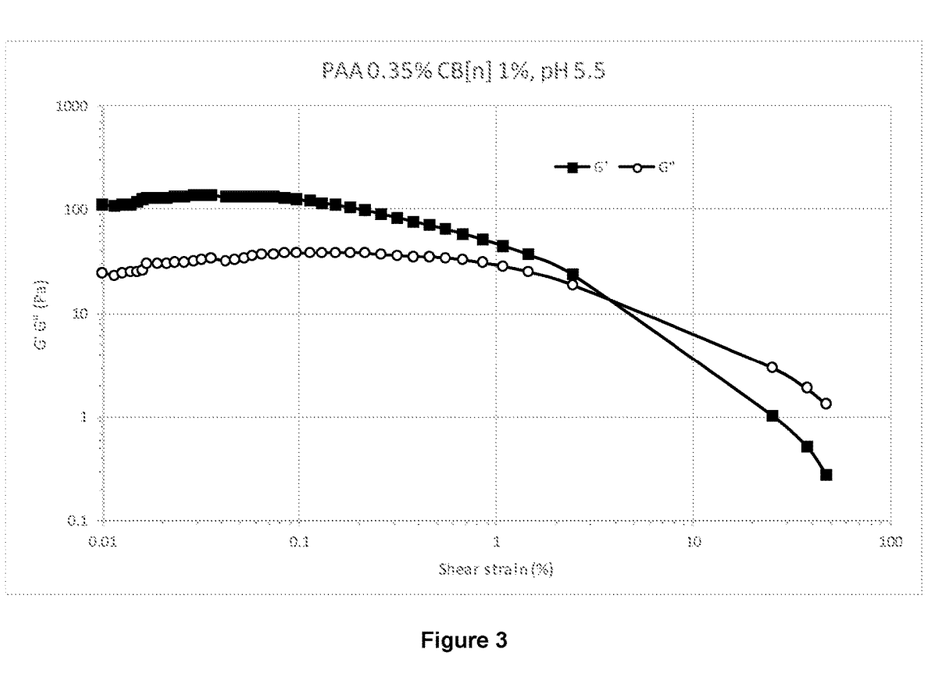
FIG. 3 shows the storage (G') and loss (G") moduli as a function of shear strain at 1 Hz for a CB[n]/polyacrylic acid suspension in water.

The following rheology data relate to the 0.35% weight PAA/1% weight CB[n] sample at pH 5.5 from Example 1.1. The shear rate sweep shows thinning behaviour over the whole range investigated (FIG. 2). The composition showed acceptable sprayability pattern when using a spray bottle with a Flairosol dispenser from Cambrian (Neck 30 Bayonet). The shear-amplitude sweeps in oscillatory flow are presented first in terms of the storage (G') and loss (G") moduli as a function of increasing shear strain at 1 Hz (FIG. 3). At low amplitude, the sample is predominantly elastic (G'≈100 Pa>G"), while above a stress of 0.744 Pa (2.48% strain datum), the value of G' falls and there is a substantial increase in strain (to 25.4% at 0.807 Pa) as sample becomes predominantly viscous (G">G'). This sharp change in properties occurs at the yield stress of ≈0.75 Pa for this sample. The behaviour is typical of that of a transient network. The stability of the suspension obtained in Example 1.1 against sedimentation is attributed to the existence of this transient network.

1.4. Malodour Suppressing Performance of Suspended CB[n] and CB[7] in PAA Systems Versus Prior Art (WO 2014/077642) Solubilised Controls (Solubilisation Performed with Phosphate Buffered Saline Tablets).

The compositions of malodours are as follows: fish (ammonia, trimethylamine and dimethylamine, each 1.5% weight in dipropylene glycol (DPG) solution), and bathroom with 0.02% U.S. Government standard bathroom malodour.

Preparation of the CB[n] suspension is as described in Example 1.1. The sample selected contained 0.35% weight PAA and 1% CB[n] at pH 5.5. The same procedure was followed for CB[7] suspended samples. For the 1% weight CB[n] and CB[7] solubilised samples, a one-gram phosphate buffered saline (PBS) tablet per 100 mL was used.

The suppressing performance of CB[n] or CB[7] malodour mixtures was investigated using a blind odour characterisation test. A six-member, trained panel characterised the odour of such compositions in terms odour intensity (using a scale of 1 to 10, with 10 being the most intense). The experiment was carried out in 1 litre glass jars covered in foil, with a small vial that contained the malodour: 80 μL of fish malodour or 100 μL of a bathroom malodour. The jars were then sprayed with 2.3 g of CB[n] or CB[7] suspensions or solutions. The odour characterisation was then carried out immediately, and after 1 and 24 hours. The results are reported in Table 4 and 5.

TABLE 4

Fish odour suppression by CB[n] solutions vs. CB[7] suspensions (average intensity ratings)

| | Initial | 1 h | 24 h |
|---|---|---|---|
| Fish Malodour | | | |
| Malodour (MO) control | 10.0 | 10.0 | 10.0 |
| MO + solubilised CB[n] | 3.0 | 5.0 | 4.8 |
| MO + suspended CB[n] | 2.4 | 1.25 | 0.4 |
| Bathroom Malodour | | | |
| Malodour (MO) control | 10 | 10 | 10 |
| MO + solubilised CB[n] | 4.4 | 6 | 6.6 |
| MO + suspended CB[n] | 2.8 | 5 | 4.8 |

It is apparent from the data in Table 4 that the ability of CB[n] to suppress fish and bathroom malodours is superior when CB[n] is suspended as opposed to solubilised.

TABLE 5

Bathroom odour suppression by CB[7] solubilised vs. CB[7] suspended (average intensity ratings)

| Bathroom Malodour | Initial | 1 h | 24 h |
|---|---|---|---|
| Malodour (MO) control | 10 | 10 | 10 |
| MO + solubilised CB[7] | 6.0 | 6.3 | 6.8 |
| MO + suspended CB[7] | 3.7 | 3.5 | 5.5 |

It is apparent from the data in Table 5 that the ability of CB[7] to suppress bathroom malodour is superior when CB[7] is suspended as opposed to solubilised.

Example 2: CB[n] Suspensions in Water with Xanthan Gum (XG) Gels (Suspending Agent)

Stable CB[n] suspensions were formulated in xanthan gum (XG) gels by carrying out the following procedure:

A 1% weight XG stock solution was prepared by adding the XG to water whilst mixing with an overhead stirrer. In a separate vessel, CB[n] was added to water to a 2% weight concentration, the mixture was then added to the XG solution at 1:1 ratio for a system with XG and CB[n] final concentrations of 0.5 and 1% respectively by weight. The XG/CB[n] mixtures were stirred with the help of an overhead mixer. The pH was then adjusted with NaOH (7M solution) to 7.0. The result was a stable sprayable translucent homogenous suspension of CB[n].

The stability of the CB[n]/XG composition was monitored as described in Example 1.2.

Example 3: CB[n] Suspensions in Hydro Alcoholic Systems

Stable CB[n] suspensions were formulated with PAA in hydro alcoholic mediums by carrying out the following procedure:

Three different hydro alcoholic mediums (aqueous compositions containing 10% weight of ethanol, methanol and isopropanol, respectively) were formulated by adding the alcohol to the first CB[n]/PAA sample described in section 1.1 while mixing with an overhead stirrer.

The stability of the CB[n]/PAA compositions in hydro alcoholic mediums was monitored as described in Example 1.2.

The invention claimed is:

1. A stable suspension composition comprising cucurbituril particles suspended in a medium, wherein the cucurbituril particles have an average particle size of from about 0.25 μm to about 50 μm.

2. The composition according to claim 1, wherein the medium is a liquid medium, an emulsion, a wax, an ointment, a gel, a paste, a foam or a liquefied gas, wherein the liquid medium is polar or non-polar, wherein when the liquid medium is polar, the liquid medium is aqueous or hydroalcoholic, wherein when the liquid medium is non-polar, the liquid medium is an oil, a paraffin, a long chain alcohol or a fat.

3. The suspension composition according to claim 2, wherein the liquid medium is selected from the group consisting of water, ethanol, n-propanol; tert-butanol; 2-methoxyethanol; 2-ethoxyethanol; 3-methoxy-3-methyl-1-butanol; isopropanol; isbutanol; 1,2-propanediol; 1,3-propanediol; 1,2-butanediol; 1,2-pentanediol; 1,2-hexanediol; 1,2-heptanediol; 1,3-butanediol; 1,4,-butanediol; 3-methyl- 1,3-butanediol; 1,4-butylene glycol; 2,3-butylene glycol; trimethylene glycol; tripropylene glycol; propylene glycol; dipropylene glycol; ethylene glycol; diethylene glycol; hexylene glycol (2-Methyl-2,4-pentanediol); mono and poly-alkylene glycols and ethers and esters thereof; glycerin; glycerin carbonate; 2,3-ortho isopropyliden glycerin; (2,2-Dimethyl-1,3-dioxolan-4-yl)methanol; alkyl lactates; alkyl lactamides; alkyl cabonates, PEG-4 (PEG-4 is also known as PEG-200); PEG-8 (PEG-8 is also known as PEG-400); PPG-14 butylether; mineral oils; paraffins, isoparaffins, glyceride esters, alkyl triglycerides; dimethicone, or a mixture thereof.

4. The composition according to claim 1, further comprising a suspending agent, wherein the suspending agent is selected from the group consisting of native or partially neutralized acrylic acid cross-polymers, methacrylic acid cross-polymers, acrylic acid-co-methacrylic acid copolymers, acrylic acic-co-methacrylic acid cross copolymers, cross-linked polymers of acrylic and/or methacrylic acid with alkyl (meth)acrylates, styrene (meth)acrylate copolymers, polyvinylpyrrolidone dimethylaminoethyl (meth) acrylate copolymers, and methacryloyl betaine acrylate copolymers, vinyl ether maleic anhydride copolymers; polyvinyl alcohol, polyvinyl pyrrolidone, sodium polystyrene sulphonate; block and graft copolymers having hydrophobic blocks and hydrophilic blocks; hydrophobic ethoxylated polyurethanes; gum *Arabicum*; gum tragacanthe; gum acacia; gum xanthan; locust bean gum; gellan gum; alginates; carrageenan; agar; modified cellulose; microcrystalline cellulose; starch alkenyl succinates; starch; vegetal fibers; pectins; gelatin; clays; and mixture thereof.

5. The composition according to claim 2, wherein the liquid medium comprises a suspending agent.

6. The composition according to claim 4, wherein the composition comprises from about 0.01 to about 25% by weight of suspending agent, based on the total weight of the composition.

7. The composition according to claim 1, wherein the pH is from about 2.0 to about 12.0.

8. The composition according to claim 1, wherein the cucurbituril is selected from CB[5], CB[6], CB[7], CB[8], or a mixture thereof.

9. The composition according to claim 1, wherein the cucurbituril particles have a mean average diameter from about 0.010 µm to about 50 µm.

10. The composition according to claim 1, wherein the composition comprises from 0.1 to 60% by weight of cucurbituril based on the total weight of the composition.

11. The composition according to claim 1, wherein the composition comprises at least 75% by weight of uncomplexed cucurbituril, based on the total weight of cucurbituril in the composition.

12. The suspension composition according to claim 1, wherein the composition has:
   a) a viscosity of between about 400 and about 1500 mPas at shear rates of about 2 $s^{-1}$ at a temperature of 20 degrees centigrade; and
   b) a viscosity of between about 10 and about 500 mPas at a shear rate between about 30 $s^{-1}$ and about 100 $s^{-1}$ at a temperature of 20 degrees centigrade; and
   c) a viscosity of between about 0.5 and about 5 mPas at a shear rate higher than 1000 $s^{-1}$ at a temperature of 20 degrees centigrade.

13. The composition according to claim 1, wherein the suspension further comprises one or more additives selected from the group consisting of surfactants, biocides, viscosifying agents, antioxidants, chelating agents, wetting agents, deposition agents, foam control agents, fragrances, solvents, dies, pigments, antiperspirant, and conditioning agents.

14. The composition according to claim 1, wherein the suspension is stable for at least three months when stored at a temperature from 4° C. to 50° C.

15. A process for the preparation of a suspension composition as defined in claim 1, comprising the steps of:
   a) adding cucurbituril particles to a medium, wherein the medium is in the liquid state;
   b) suspending the cucurbituril particles in the medium under high shear conditions.

16. A method of counteracting malodour comprising applying to a source of malodour a suspension composition as defined in claim 1,
   wherein the composition is applied to an inanimate surface,
   wherein the composition is applied by spraying,
   wherein the source of malodour is selected from the group consisting of human or animal sweat, faeces or urine; wet pet; mould; food or a combination thereof,
   wherein the composition is contained in a consumer product.

17. A method comprising applying a suspension composition as defined in claim 1, for counteracting malodour.

18. The method according to claim 17, wherein the malodour is a nitrogen-containing molecule, a sulphur-containing molecule or an oxygen-containing molecule.

19. The method according to claim 17, wherein the suspension composition is contained in a consumer product.

20. A method of re-suspending a composition comprising agitation of a composition comprising cucurbituril particles in a medium, to obtain the suspension composition as defined in claim 1, whereby agitation re-suspends any particle sedimentation.

21. A consumer product comprising a suspension composition as defined in claim 1, wherein the consumer product is selected from the group consisting of a pet care product, a fabric care product, a hair or skin or homecare cleansing composition, a softener, a softener sheet, a conditioner, a fabric refresher, an air freshener, a deodorizing composition, a personal deodorant, an antiperspirant, a cosmetic product, a fine fragrance, a body mist, a candle, a cleansing wipe or mop, a soap, a styling gel, a humidity absorber, an air filtration device, a fabric finishing product, a diaper or sanitary product, a shoe sole, a denture bath, a wound dressing, a pet litter and a chemical toilet.

22. Granules or beads coated with the composition according to claim 1.

23. Granules or beads according to claim 22, wherein uncoated granules or beads have an average particle size of between 0.1 and 10 mm.

24. A method for producing the granules or beads according to claim 22, the method comprising the step of spraying uncoated granules or beads or blending uncoated granules or beads with the composition comprising cucurbituril particles suspended in a medium.

* * * * *